United States Patent [19]

Panster et al.

[11] Patent Number: 5,187,134
[45] Date of Patent: Feb. 16, 1993

[54] FORMED, POLYMERIC TRANSITION-METAL COMPLEX CATALYSTS WITH ORGANOSILOXANE PHENYLPHOSPHINE LIGANDS

[75] Inventors: Peter Panster, Rodenbach; Robert Gradl, Alzenau, both of Fed. Rep. of Germany

[73] Assignee: Degussa AG, Hanau, Fed. Rep. of Germany

[21] Appl. No.: 784,951

[22] Filed: Nov. 1, 1991

[30] Foreign Application Priority Data

Nov. 3, 1990 [DE] Fed. Rep. of Germany ....... 4035032

[51] Int. Cl.$^5$ ............................................. B01J 31/24
[52] U.S. Cl. ..................................... 502/158; 502/8; 502/9; 502/166; 502/167
[58] Field of Search .................... 502/9, 8, 158, 166, 502/167

[56] References Cited

U.S. PATENT DOCUMENTS

| | | | |
|---|---|---|---|
| 3,907,852 | 9/1975 | Oswald et al. | 502/162 X |
| 4,067,820 | 1/1978 | Wagner et al. | 502/162 X |
| 4,276,195 | 6/1981 | Verkade | 502/167 X |
| 4,424,332 | 1/1984 | Panster et al. | 528/30 |
| 4,442,040 | 4/1984 | Panster et al. | 260/429 R |
| 4,482,752 | 11/1984 | Mitchell et al. | 502/167 X |
| 4,520,122 | 5/1985 | Arena | 502/162 X |
| 4,645,847 | 2/1987 | Panster et al. | 556/9 |
| 4,647,679 | 3/1987 | Panster et al. | 556/9 |
| 4,657,884 | 4/1987 | Luft et al. | 502/167 X |
| 4,845,163 | 7/1989 | Panster et al. | 525/475 |
| 4,895,817 | 1/1990 | Ogata | 502/162 X |
| 4,999,413 | 3/1991 | Panster et al. | 528/30 |
| 5,003,024 | 3/1991 | Panster et al. | 528/30 |
| 5,093,451 | 3/1992 | Panster et al. | 528/9 |
| 5,094,831 | 3/1992 | Klockner et al. | 425/342 |

FOREIGN PATENT DOCUMENTS

| | | |
|---|---|---|
| 0072435 | 2/1983 | European Pat. Off. . |
| 0151991 | 8/1985 | European Pat. Off. . |
| 2330308 | 1/1974 | Fed. Rep. of Germany . |
| 3029599 | 2/1982 | Fed. Rep. of Germany . |
| 3050815 | 2/1982 | Fed. Rep. of Germany . |
| 3518880 | 11/1986 | Fed. Rep. of Germany . |
| 3643894 | 6/1988 | Fed. Rep. of Germany . |
| 3837418 | 5/1990 | Fed. Rep. of Germany . |
| 3925359 | 2/1991 | Fed. Rep. of Germany . |

OTHER PUBLICATIONS

R. H. Grubbs, "Hybrid-Phase Catalysts," in *Chemtech*, Aug. 1977, pp. 512-518.

Ejike, E. N., et al., "Insoluble Poly(alkylarylphosphine) Siloxanes and Their Applications as Supports for Catalytic Transition-Metal Complexes" 0 Journal of Applied Polymer Science, vol. 38 (1989) pp. 271-280.

Parish, R. V., et al., "Insoluble Ligands and Their Applications II-Polysiloxane-Phosphine Ligands, Their Complexes and Hydrogenation Catalysts," Journal of Organometallic Chemistry, vol. 369 (1989) pp. 17-18.

*Primary Examiner*—Patrick P. Garvin
*Attorney, Agent, or Firm*—Beveridge, DeGrandi, Weilacher & Young

[57] ABSTRACT

This invention relates to formed, polymeric complexes of metals of the eighth subgroup of the periodic system with ligands of an organosiloxane copolycondensate optionally cross-linked by means of cross-linking agents containing Si, Ti, Zr and/or Al, in the form of statistical, block or mixed copolycondensates. The ratio between the number of moles of phosphine units and the number of moles of bound metal atoms is 1:1 to 1000 to 1 and the ratio between the amine units and the phosphine is preferably 5:95 to 95:5 mole %. The polymeric complex compounds are present macroscopically as spherical particles with a diameter in the range of 0.01 to 3.0 mm, a BET surface of greater than 0 to 1000 m$^2$/g, a specific pore volume of 0.01 to 6.5 ml/g and a bulk density of 50 to 1000 g/l. The invention also includes several methods of preparing the complexes with post-treatment stages and the use of the polymeric metal complexes as catalysts in organic chemistry.

29 Claims, No Drawings

FORMED, POLYMERIC TRANSITION-METAL COMPLEX CATALYSTS WITH ORGANOSILOXANE PHENYLPHOSPHINE LIGANDS

BACKGROUND OF THE INVENTION

The subject matter of the invention relates to a polymeric transition-metal complex catalyst with organosiloxane phenylphosphine ligands which are present as formed copolycondensates. The formed, polymeric, insoluble complex compounds of Fe, Co, Ni, Ru, Rh, Pd, Os, Ir and/or Pt exhibit the engineering and application-technology advantages of a macroscopic spherical form and have the physical properties necessary for use as a heterogenized complex catalyst. Additionally, methods are described herein whereby the products can be prepared, not only in the spherical size desired for the particular use, but also with the suitable physical properties. In addition, the use of these polymeric catalysts is described.

Homogeneous catalysts that are used exhibit, without exception, a higher activity and selectivity than comparable heterogeneous catalysts. However, rather significant engineering problems generally occur in the use of these catalysts in connection with their separation of the formed product from solvent present and with their recycling. Moreover, the recovery of the expensive noble-metal component from the residue of the reaction mixture is expensive and can normally only be carried out only with rather significant metal losses.

In many instances, another disadvantage of homogeneous catalysts that are used is the rather short residence time, which is caused by the formation of catalytically inactive species.

In order to circumvent these disadvantages of the homogeneous catalysts, so-called "heterogenized homogeneous catalysts" or "heterogenized catalysts" have been developed. In these catalyst, the normally homogeneous catalyst is bound to a solid carrier. These catalysts have already been used for some time worldwide.

The state of the art in this area of catalysis has already been multiply summarized in the appropriate survey literature, e.g. by R. H. Grubbs in CHEMTECH, August 1977, p. 512; by F. R. Hartley in "Catalysis by Metal Complexes", D. Reidel Publ. Co., 1985; or also by Yu. I. Yermakov et al. in "Catalysis by Supported Complexes", Elsevier Scientific Publ. Co., 1981. These literature citations are entirely incorporated herein by reference.

However, up to the present time, for a number of reasons, the organic and inorganic polymer systems used as carrier materials have met the desired requirements only to a very limited extent. In particular, in the case of the organic polymer carriers, the physical and mechanical properties, as well as the unacceptably low chemical stability, represent disadvantages. With regard to the inorganic polymer carriers, such as silica gel, these carriers have the disadvantage of a low ability to be functionalized and, in addition, are insufficiently defined.

Novel, heterogenized metal complex catalysts which do not exhibit these disadvantages of the previous systems were recently developed, as in described in German patent 30 29 599, which is entirely incorporated herein by reference. The matrix of these polysiloxane catalysts practically has the advantages of an inorganic polymer carrier and, in addition, can be produced approximately on a made to order basis in accordance with the requirements of the particular system. For example, with regard to the important aspects of the catalysts, the metal:ligand ratio can be varied; the crosslinking agents can be integrated into the matrix; or the catalytic central density and distribution can be controlled. Compared to systems with purely inorganic carriers, these organopolysiloxane polymers display the advantages of a higher metal concentration, a simpler preparative accessibility and a greater stability vis-a-vis chemical degradation.

In particular, the polymeric metal phosphine complexes mentioned in German patent 30 29 599, which generally exhibit very good catalytic properties, were synthesized according to this concept. However, these heterogenized complex catalysts have the disadvantage that previously they could be prepared only in a relatively undefined macroscopic shape, and not in the spherical form advantageous in application technology, with the desired physical and morphological properties.

SUMMARY OF THE INVENTION

It is an object of the present invention to provide a method of preparing heterogenized transition-metal complexes with organosiloxane phenylphosphine ligands in spherical form and with the desired physical properties in a reproducible manner.

The invention includes formed, spherical, polymeric metal complexes of iron, cobalt, nickel, ruthenium, rhodium, palladium, osmium, iridium and/or platinum. The complexes are characterized in that the ligands include a spherically formed, organosiloxane copolycondensate having units of the formula

and of units of the formula

In the complexes, the central metal atom is coordinatively bound via the strongly bonding phosphorus atoms of the phosphine units (II) or, additionally, via the more weakly bonding nitrogen atoms of the amine units (I). $R^2$ to $R^5$ represent the same or different groups and signify a group of the formula

in which $R^6$ is bound directly to the phosphorus atom or to the nitrogen atom, and it further represents a linear or branched alkylene group with 1 to 10 carbon atoms, a cycloalkylene group with 5 to 8 carbon atoms or a unit of the formula

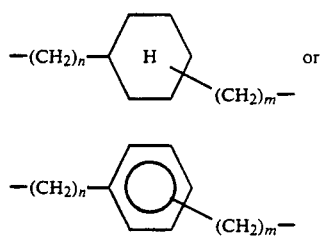

in which "n" and "m" are a number from 0 to 6, wherein "n" indicates the number of methylene groups bound to the N position or bound to the P position, and m indicates the number of methylene groups bound to the Si position. $R^1$ also represents a group of formula (III) or stands for H, $CH_3$, $C_2H_5$, $C_3H_7$. The free valences of the oxygen atoms bound to the Si atom are saturated as in silica skeletons by silicon atoms of further groups of formula (III) and/or via the metal atoms in one or several cross-linking bridge members

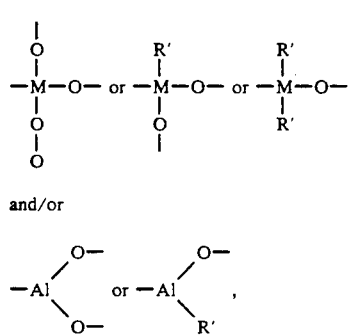

(IV)

and/or wherein M is an Si, Ti or Zr atom and R' is a linear or branched alkyl group with 1 to 5 carbon atoms or a phenyl group, and the ratio of the silicon atoms from the groups of formula (III) to the metal atoms in the cross-linking bridge members (IV) is 1:0 to 1:20 and the ratio between the number of moles of phosphine units (II) and the number of totally complex-bound metal units is 1:1 to 1000:1, preferably 1:1 to 100:1, and the polymeric complex catalysts are present macroscopically as spherical particles with a diameter of 0.01 to 3.0 mm, preferably 0.05 to 2.0 mm, a BET specific surface of greater than 0 to 1000 m²/g, preferably greater than 0 to 700 m²/g, with a specific pore volume of 0.01 to 6.5 ml/g, as well as with a bulk density of 50 to 1000 g/l, preferably 100 to 700 g/l.

It has proven to be especially advantageous within the framework of the invention, both with respect to the preparation and the physical properties, as well as with regard to the catalytic properties of the heterogenized complex catalysts as a polymer ligand system, to use a copolycondensate with amine groups and phosphine groups. Certain copolycondensates have been described in German Patent Publication DE-OS 39 25 359.7, which application corresponds to U.S. patent application Ser. No. 07/556,486, filed in the United States on Jul. 24, 1990, which documents are entirely incorporated herein by reference.

The ratio of units according to formula (I) to units according to formula (II) can vary greatly and can be within the limits of 5:95 to 95:5 mole %. Problems with the morphological, physical and chemical properties of the polymeric complex catalysts of the invention are thereby eliminated.

One particular embodiment of the invention provides that the $R^1$ to $R^5$ groups are a group of the formula (III) and are identical or different.

The ratio to be selected in practice depends primarily on the complex to be prepared, as well as on the intended area of use and the chemical and physical properties required for the complex, e.g., depending upon whether a high metal concentration or a high density of the phosphine component or the amine component is required to provided the necessary catalytic properties or the metal adhesion.

The monomeric structural elements of the formed polymer ligand system are basically known compounds, e.g., compounds of the formulas:
$N[(CH_2)_3Si(OC_2H_5)_3]_3$
$N[(CH_2)_{10}Si(OCH_3)_3]_3$
$C_6H_5-P[(CH_2)_3Si(OCH_3)_3]_2$
$Si(OC_2H_5)_4$, $(H_3C)_2Si(OC_2H_5)_2$
$Ti(OC_3H_7)_4$ The composition of the polymer units obtainable from them can be described by the formulas
$N[(CH_2)_3SiO_{3/2}]_3$
$N[(CH_2)_{10}SiO_{3/2}]_3$
$C_6H_5-P[(CH_2)_3SiO_{3/2}]_2$
$SiO_{4/2}$, $(H_3C)_2SiO_{2/2}$
$TiO_{4/2}$ The spherically shaped copolycondensates may be present even in the case of the same chemical composition in completely different forms, such as the so-called "statistical copolycondensates" (or "random copolycondensates"), or the "block copolycondensates" or also the so-called "mixed copolycondensates." According to the invention, the formed polymer ligand systems can be present as the units according to formulas I, II and IV in each of the three named forms. This means that in the case of a purely statistical copolycondensate containing units according to formulas I and II and optionally IV, there is a statistical distribution of the components according to the molar ratios of the initial products, taking into consideration the silicon groupings present in the case of units I and II according to formula III and the functionality of the cross-linking agent grouping IV.

In the case of a block copolycondensate, there is a formation of blocks of identical units according to formulas I and II and optionally IV.

Finally, a mixed copolycondensate exhibits both structures of a statistical copolycondensate, as well as structures of a block copolycondensate. The units according to formula I or formula II or formula IV may be present both as statistical copolycondensates and also block copolycondensate.

Particular advantages with regard to the availability of the initial materials and the material properties are achieved with polymer ligand systems in which $R^1$ to $R^5$ stand for a group of the formula:

(V)

The preferred metal-containing groups which are bound in a complex manner to the polymer units according to formula II and formula I are one or several metal units VI of:

$FeX_3$, $FeX_2$, $CoX_3$, $CoX_2$, $NiX_2$, $RuX_3$, $RuX_2$, $RhX_3$, $RhX_2$, $RhX$, $Rh(dien)X$, $RhX(CO)$, $PdX_4$, $PdX_2$, $Pd^0$, $OsX_3$, $IrX_3$, $IrX$, $Ir(dien)X$, $IrX(CO)$, $PtX_4$, $PtX_2$, and $Pt^0$, in which X stands for Cl, Br, I, H, acetyl acetonate, acetate, 0.5 $SO_4$, $NO_3$, and CN, and dien stands for cyclooctadiene or norbornadiene.

The complex structures formed by complex formation between metal units and polymer ligand system are basically known from the complex chemistry of these metals and are familiar to the chemist skilled in the chemistry of complexes (Cf., e.g., the book series "Inorganic Syntheses", John Wiley & Sons, New York, Chichester, Brisbane, Toronto, Singapore, or "Inorganic Chemistry of the Transition Elements", Chemical Society, Burlington House, London W1V OBN).

They can be described for the individual metals relevant to the invention, for example, by the following formulas:

$FeX_3L_3$, $FeX_2L_4$, $CoX_3L_2$, $CoX_3L_3$, $CoX_2L_3$, $CoX_2L_4$, $NiX_2L_2$, $NiL_4$, $RuX_3L_3$, $RhX_3L_3$, $RhX_2L_3$, $RhXL_3$, $RhL_4^+X^-$, $PdX_4L_2$, $PdX_2L_2$, $PdL_4$, $OsX_3L_3$, $IrX_3L_3$, $IrXL_3$, $PtX_4L_2$, $PtX_2L_2$, and $PtL_4$, wherein X=Cl, BR, I, H, acetyl acetonate, acetate, $\frac{1}{2}SO_4$, $NO_3$, or CN, and L=ligand.

The soluble complex structures known from the complex chemistry of these metals also may naturally be transferred onto the polymer-ligand-bound, insoluble metal units. This means that in the case of the formed transition-metal complex catalysts of the invention, L represents a polymer ligand unit of formula I or formula II, which represent the anchor groups via which the previously named metal units are bound to the polymer matrix.

In the case of the heterogenized complex catalysts in accordance with the invention, advantageous catalytic properties are realized if the above-named metal units according to formula VI are bound to the polymer matrix via at least one phosphine unit according to formula II in each instance.

A preferred embodiment of the invention provides that the metal units according to formula VI are bound in each instance to the polymer matrix only via phosphine units according to formula II.

It is advantageous for the practice of this invention if the metal content in the polymer system is at least 0.01% by weight and at the most 20% by weight, and preferably, 0.1% to 10% by weight.

Regarding the catalytic properties and the metal adhesion of the compounds of the invention, the phosphine units according to formula II are the decisive ligand components in the building of the polymeric metal-matrix compound, whereas the amine groupings assure the particular advantageous physical properties, and, in part, also the chemical properties of the polymer.

The composition of the compounds of the invention may be influenced via certain production measures. For example, the distribution of the two ligand types according to formulas I and II resulting from the process may be influenced depending upon their stoichiometric ratio. It is basically known from complex chemistry that a phosphine ligand of the type of the ligand unit according to formula II (type: dialkylphenylphosphine) exhibits a considerably stronger complexing capacity than an amine ligand of the type of the ligand unit according to formula I. This fact must be taken into account in the conception of the polymeric metal complexes to be built up and in the selection of the production measures, because as a rule, the phosphine ligand will always complex the central atom of the transition metal with precedence in the case of a competing situation.

The metal concentrations indicated take into account the fact that, in addition to the ligands according to formulas II and I complexing the fixed metal centers according to formula VI, still other excess and non-complexing ligands according to formulas I and/or II are present in the polymer system. A special embodiment of the invention provides that no more ligand units according to formula II are present in the polymer system than are maximally required to build up the particular metal complex, so that the stoichiometric ratio between the ligands according to formula II and the metal is at least 1:1, but, as a function of the particular metal chosen, i.e., for Fe, Co, Rh, Pd, Pt, and Ni, a maximum of 4:1 and for Ru, Os, and Ir a maximum of 3:1, and that other ligands according to formula I also are present in the polymer system. In the case of a ratio of 1:1, amine units according to formula I also must be used for building up the polymeric metal complex.

It may be advantageous in a number of polymeric catalysts, as a function of the type of the reaction to be catalyzed (e.g., the obtention of an improved metal adhesion or of improved selectivity properties), if excess polymer ligand units according to formula II above the ratio of 4:1 or 3:1 also are present in the polymer matrix. These excess ligands according to formula II also may be present in relation to the amine units according to formula I and the optionally present crosslinking agents, both as statistical, block or mixed copolycondensates.

On the whole, the extreme values of the conceivable compositions are given, on the one hand, by the limit values of the molar ratio of the units according to formula I to the units according to formula II, i.e., 95:5 mole % to 5:95 mole %, and on the other hand, by the possible metal contents of 0.01 to 20% by weight.

In addition, the invention includes methods of preparing the formed, polymeric transition-metal complex catalysts of the invention. The initial metal compounds used are almost exclusively those which are relatively readily accessible from a preparative standpoint and are commercially available. The preparation of the monomer complex which proceeds the polycondensation stage, that is, the formation of the polymer matrix, and which uses silicon-substituted monomer ligands of the formula

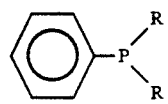

and optionally of the formula

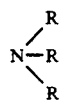

takes place in these methods of the invention according to known principles of transition-metal chemistry like those described in a general manner in the previously cited literature or in scientific publications on the complex chemistry of the metals named here.

A first method of preparing the formed polymeric metal complexes in accordance with this invention is characterized in that one or several hydrous or anhydrous metal compounds VII of:

$FeX_3$, $FeX_2$, $CoX_3$, $CoX_2$, $NiX_2$, $RuX_3$, $RuX_3(CH_3CN)_3$, $RuX_3(C_6H_5CN)_3$, $M_3RhX_6$, $RhX_3$, $RhX_3(CH_3CN)_3$, $RhX_3(C_6H_5CN)_3$, $RhX_2$, $[RhX(dien)]_2$, $M_2PdX_6$, $M_2PdX_4$, $PdX_2$, $OsX_3$, $OsX_3(CH_3CN)_3$, $OsX_3(C_6H_5CN)_3$, $M_3IrX_6$, $IrX_3$, $IrX_3(CH_3CN)_3$, $IrX_3(C_6H_5CN)_3$, $[IrX(dien)]_2$, $M_2PtX_6$, $M_2PtX_4$, and $PtX_2$, in which X=Cl, Br, I, acetyl acetonate, acetate, $\frac{1}{2}SO_4$, $NO_3$, or CN; diene=cyclooctadiene or norbornadiene (also known as (2,5)norbornadiene or Bicyclo[2,2,1-]hepta-2,5-dien; $C_7H_8$, having a molecular weight of 92.14 and a boiling point in the range of 88°–90° C.); and M=H, Na, K, or $NH_4$, are reacted to form the metal complex in a solvent or a solvent mixture with a preferably polar nature, optionally at an elevated temperature, for a period of 1 minute to 48 hours with a phosphine of the formula:

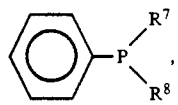 (VIII)

in which $R^7$ and $R^8$ are identical or different and signify a group of the formula:

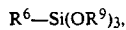 (IX), wherein $R^6$ has the same meaning as in formula III, $R^9$ signifies a linear or branched alkyl group with 1 to 5 carbon atoms, and the ratio between the number of moles of phosphine according to formula VIII and the number of moles of the total complex bound metal atoms in the metal compounds according to formula VII is at least 1:1 to 1000:1, and preferably 1:1 to 100:1. Thereafter, an amino silane of the formula:

 (X)

is added to the solution, wherein $R^{10}$ stands for H, $CH_3$, $C_2H_5$, $C_3H_7$ or a group of formula IX and $R^{11}$ and $R^{12}$ also stand for a group of formula IX in which $R^6$ and $R^9$ have the same range of meaning as in formula IX, and optionally one or several compounds of the formula:

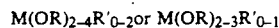 (XI)

in which M is an Si, Ti, Zr or Al atom, R' is a linear or branched alkyl group with 1 to 5 carbon atoms or a phenyl group, R signifies a linear or branched alkyl group with 1 to 5 carbon atoms and the ratio of the silicon atoms from the groups of formula IX to the metal atoms in the cross-linking agents IX is 1:0 to 1:20. Then an amount of water is added to the obtained solution under agitation which suffices at least for a complete hydrolysis and condensation. The reaction mixture is hydrolysed for a period of up to 6 hours, preferably at reflux temperature, then allowed to gel under further agitation at a temperature in the range of room temperature to 200° C. on the condition that it is compounded at the start of gelling or up to one hour thereafter with 10 to 2000, preferably 50 to 500% by weight (relative to the entire amount of phosphine (VIII), aminoorganosilane (X) and, optionally, cross-linking agent (XI)), with a solvent which is largely non-water-soluble but dissolves the reaction mixture which has gelled or started to gel. The reaction mixture is thereby homogenized, and 10 to 2000%, preferably 50 to 500% by weight (relative to the total amount of phosphine (VIII), aminoorganosilane (X) and, optionally, cross-linking agent (XI)) water is added to the viscous homogenizate immediately or in a time period of up to 10 hours, optionally under elevation of the originally adjusted temperature. The organic phase containing the monomeric metal complex is dispersed in the liquid two-phase system and the solid forming in the form of spheres is separated from the liquid phase after a reaction time sufficient for this purpose at a temperature in the range of room temperature to 200° C., then extracted, optionally with a low-boiling solvent, dried at room temperature to 250° C., optionally under protective gas or in a vacuum and tempered 1 to 100 hours at temperatures of 150° C. to 300° C. and/or classified.

According to this first method of the invention, mixed or statistical copolycondensates are obtained as a function of the stoichiometry in relation to all of the polymer units according to formulas I and II present, as well as, optionally, according to the groups according to formula IV present. It should be noted that a block formation takes place on the metal center on account of the complexing of the phosphine units according to formula II and, when hydrous metal compounds (VII) are used, a partial precondensation of the added monomeric phosphines according to formula VIII already takes place during their reaction with the metal component. However, when anhydrous metal compounds (VII) are used, the formation of a statistical distribution is to be assumed for phosphine units according to formula II, which are optionally present above the highest coordination number and in relation to non-complexing or slightly complexing amine ligands (I), as well as any cross-linking groups (IV) which are optionally present.

Instead of the alkoxy silyl compounds, the corresponding halogenide or phenoxy compounds also may be used, in principle, as the initial materials for the method; however, their use offers no advantages, but rather can cause problems. For example, in the case of the chlorides, problems may arise as a result of the hydrochloric acid liberated during hydrolysis.

The hydrolysis of the initial materials and the optional the cross-linking agent or agents is most preferably carried out in a solvent which is miscible with water to a great extent, but which also dissolves the initial materials. Alcohols are preferably used which correspond to the alkoxy groupings on the monomeric precursors of the initial materials or on the metal atoms of the optionally used cross-linking agents.

Methanol, ethanol, n-propanol, i-propanol, n-butanol, i-butanol or n-pentanol are especially suitable. Mixtures of such alcohols also may be used. Instead of alcohols, other polar solvents which are miscible with water to a great extent also may be used; however, this is not very logical for engineering reasons because the solvent mixtures which are produced with the alcohol hydrolytically split off.

The hydrolysis is preferably carried out with an excess of water above the stoichiometrically required amount. The amount of water necessary for hydrolysis depends on the hydrolysis speed of the phosphine (VIII), amine (X) and cross-linking agent (XI) used in such a fashion that as the amount of water increases, a more rapid hydrolysis occurs; however, an upper limit can be given due to separation and the formation of a two-phase system. Due to the two aspects cited, somewhat less water by weight is used in practice than the organosilanes plus cross-linking agent. The duration of the hydrolysis is a function of the tendency to hydrolyze, of the initial substances and/or cross linking agents, and of the temperature. The readiness for hydrolysis and therewith the hydrolysis speed is especially a function of the type of the alkoxy groups in the silicon or titanium, zirconium and aluminum position; the methoxy group hydrolyses the most rapidly thereby. In addition, the duration of the total process of hydrolysis and polycondensation is also a function of the basicity of the aminoorganosilane. As is known, amines function as condensation accelerators, so that they can bring about a self-catalysis.

Hydrolysis and polycondensation are generally accelerated by the addition of bases, preferably ammonia, or by the addition of inorganic or organic acids. These reaction rates also may be accelerated by the catalytically active metal itself, or by the addition of customary condensation catalysts, such as dibutyl tin diacetate.

The requirement of maintaining the initial substance, which is dissolved in solution and compounded with water, at a certain temperature under continuing agitation, therefore, has the result that the speed of the polycondensation, indicated by gelling, is temperature-dependent.

The temperature to be used in the hydrolysis phase or gelling phase is determined empirically and is set in each individual instance. It should be selected in such a manner that a gel-like mass is retained in the following method step, the so-called "forming phase."

The forming phase, which proceeds with the conversion of the coherent, metal-containing, gel-like mass permeated by liquid into separate, spherical particles, begins with the compounding of the reaction mixture which has gelled or started to gel with a solvent in the provided amount which is largely non-water-soluble, but dissolves the reaction mixture to a sufficient extent.

Suitable solvents are, for example, linear or branched alcohols with 4 to 18 carbon atoms; phenols; linear or branched symmetric or asymmetric dialkyl ethers, as well as diethers or triethers (such as ethylene glycol dimethyl ether); chlorinated or fluorinated hydrocarbons, aromatics or mixtures of aromatics substituted with one or several alkyl groups, such as toluene or xylene; and symmetric or asymmetric ketones which are largely non-miscible with water.

However, a linear or branched alcohol with 4 to 12 carbon atoms, toluene, ethyl benzene or o-xylene, m-xylene, p-xylene or mixtures thereof preferably are added to the reaction mixture which has gelled or started to gel.

The addition of solvent brings about, after the homogenization with the reaction mixture, a dilution and therewith a distinct slowing of the condensation reaction with the increase in viscosity.

The measuring of the amount of this solvent used in the forming phase depends in particular on which grain size is desired for the formed, polymeric transitional-metal complex catalyst. It can be considered a rule of thumb that little solvent is to be used for coarse grain (i.e., spheres with a fairly large diameter) and more solvent is to be used for fine grain (spheres with a rather small diameter). In addition, the intensity with which the viscous homogenizate of the forming reaction product and the largely non-water-soluble solvent is dispersed in the aqueous phase also influences the grain size. The formation of a rather fine grain is favored by vigorous agitation. In order to stabilize the aqueous dispersion of the organic phase containing siloxane, one of the known dispersing agents, such as long-chain carboxylic acids or their salts or polyalkylene glycols, may be added in customary concentrations.

The preferred temperature at which the dispersion of the organic phase containing siloxane is carried out in the aqueous phase, and at which spherical solid is formed from the dispersed phase, is, as a rule, the reflux temperature of the entire mixture. Basically, however, the same temperatures as in the gelling stage can be used. The total time of the dispersing stage and post-reaction is, as a rule, 0.5 to 10 hours.

Both the gelling and the forming may be carried out at normal pressure or at a superpressure which corresponds to the sum of the partial pressures of the components of the reaction mixture at the particular temperature used.

The separation of the spherically formed, moist product from the liquid dispersing agent may take place by means of customary measures such as decanting, filtering off or centrifuging. In addition, however, the liquid phase may also be removed from the reactor and the remaining solid in it treated once or several times with a low-boiling extraction agent, preferably a low-boiling alcohol, in order to facilitate the later drying of the formed catalyst by means of an at least partial exchange of the usually relatively high-boiling solvent of the forming phase with the low-boiling extraction agent.

The drying may be carried out at room temperature to 250° C., optionally under a protective gas or in a vacuum. For hardening and stabilizing, the dried, formed solid can be tempered at temperatures of 150° to 300° C.

The dried and/or tempered product can be classified in customary devices into various grain size fractions. One or more of the other of the workup measures, such as, extraction, drying, tempering and classification may be eliminated, depending on the circumstances. The classification may be carried out on liquid-moist, dry or tempered product.

According to a variation on the method of the invention, a part or the entire amount of the solvent, which is largely non-water-soluble and is to be added at or after the initiation of gelling, is added to the reaction mixture already in the hydrolysis stage, in addition to the solvent used in it. In the case of a partial addition, the remainder of the solvent is added after the start of gelling. In the extreme case of the addition of the entire amount of the solvent, the dispersing agent water can be added at or after the start of gelling. This variant is preferably used when the mixture of the Si-substituted monomer complex prepared and of the optionally present, excess phosphine according to formula VIII and amine (X) as well as the optional cross-linking agents (XI) exhibits an extraordinarily high tendency toward hydrolysis and polycondensation.

With respect to the adjustment and fixing of a certain defined ligand sphere around the polymer-bound metal center, it can be especially advantageous if, in accordance with a variation of the method described above, the monomeric phosphine complex obtained after reaction with the phosphine according to formula VIII with the metal compound according to formula VII and the excess phosphine amount according to formula VIII, which is optionally still present in the mixture and is not required for complex formation, are at first precondensed up to the maximum ratio of phosphine (VIII) to metal compound (VII) of 1000:1, optionally after the addition of one or several of the compounds of formula XI. To this end, one or several hydrous metal compound(s) of formula VII in a preferably polar solvent or solvent mixture is (are) reacted with a phosphine of formula VIII at a ratio between the number of moles of phosphine units (VIII) and the number of moles of the totally complex-bound metal atoms of 1:1 to 1000:1, preferably 1:1 to 100:1 for a period of 1 minute to 48 hours, a part or the complete amount of one or several of the compounds of formula XI is optionally added to the solution of the formed, monomeric metal complex. This mixture is precondensed in the presence of an amount of water insufficient for complete hydrolysis, preferably from 1 to 100 mole % of the amount required for this, for a period of 5 minutes to 48 hours at a temperature in the range of room temperature to 200° C. Then an amino silane of formula X, optionally the remaining or complete amount of one or more of the compounds according to formula XI, optionally more solvent, and, in any case, more water is added. The mixture is hydrolyzed again for a period of up to 4 hours, preferably at the reflux temperature of the reaction mixture, and then the procedure described above is followed with respect to gelling and the further treatment of the condensate which forms thereby.

The precondensation can generally be accelerated by the addition of a slight amount of an acidic or basic or metal-containing condensation catalyst.

Suitable catalysts are inorganic or organic acids or bases or also tin compounds. The amount of water used for precondensation depends on which degree of oligomerization, that is, which block size, is to be achieved. When more water is used for the precondensation, larger units naturally are produced than when less water is used. An amount of water introduced by an initial metal component according to formula VII containing water of crystallization must, of course, also be considered in this connection when selecting the amount of water used for precondensation. According to a variation of this method of the invention, the addition of free water is eliminated in the precondensation, and it is carried out only with the water introduced by the metal component (VII) containing water of crystallization.

According to a further variation on this method, the amount of water used for precondensation and exceeding the optionally present amount of water of crystallization is added right at the start of the reaction of the metal component (VII) with the phosphine (VIII) so that the formation of the monomer complex and its precondensation, the precondensation of the excess ligands, as well as that of the optionally added compound(s) according to formula XI, take place simultaneously. The complete hydrolysis and condensation are carried out directly thereafter.

The duration of precondensation generally depends, as already described above, on the readiness for hydrolysis of the monomeric components and the temperature.

A second method of the invention provides that one or several hydrous or anhydrous metal compounds of formula VII are reacted for a period of 1 minute to 48 hours in a preferably polar solvent with a phosphine of the formula VIII in a ratio between the number of moles of phosphine units (VIII) and the number of moles of the totally complex-bound metal atoms of 1:1 to x:1, where x represents the particular metal-specific maximum coordination number in the particular metal complex. A part of or the complete amount of one or several of the compounds of formula XI is optionally added to the solution of the monomeric metal complex formed and this mixture is precondensed in the presence of an amount of water insufficient for complete hydrolysis, preferably from 1 to 100 mole % of the amount required for complete hydrolysis, for a period of 5 minutes to up to 48 hours at room temperature to 200° C. Thereafter, the amount of phosphine of formula VIII exceeding the maximum coordination number of the metal, optionally the remaining or complete amount of one or several of the compounds according to formula XI, as well as an amino silane of formula X, optionally more solvent, and in any case, more water are added. The mixture is hydrolyzed again for a period of up to 4 hours, preferably at the reflux temperature of the reaction mixture, and then one of the procedures or variations described above in the first method in accordance with the invention is carried out.

Of course, in this and in all subsequent precondensation variants, an acidic, basic or metal-containing condensation catalyst also may be added or the precondensation may be carried out only with the water of crystallization of a hydrous initial metal compound or the precondensation can be carried out parallel in time with the reaction of the metal component (VII) with the phosphine (VIII).

A third method of the invention includes the formation of block copolycondensates. In the block copolycondensates, there is a formation of blocks of the same units according to formulas I and II and optionally of one or several units according to formula IV. The monomeric metal complex obtained from the reaction of the metal compound of formula VII with the phosphine component of formula VIII (as described in the first and second methods above) is precondensed together with any optionally present, excess phosphine (VIII) during or after its preparation and an amino silane of formula X, as well as, optionally, one or several compounds of formula XI for a period of 5 minutes to 48 hours at room temperature to 200° C., independent of each other, with or without a solvent and in the presence of an amount of water insufficient for complete hydrolysis, preferably in the presence of 1 to 100 mole % of the amount required for this. Thereafter, the individual precondensed components are combined and then, after the addition of water such that at least the amount of water stoichiometrically necessary for a complete hydrolysis is present and, optionally, after more solvent, the complete hydrolysis and polycondensation as well as any further workup are carried out, as described in the first method in accordance with the invention.

A fourth method of the invention is intended to compensate in particular a distinctly different gelling behavior of the formed metal complex containing phosphine groups and of the optionally present, excess phosphine (VIII), on the one hand, and of the amino silane (X), as well as of one or several compounds (XI), on the other hand. This method provides that the metal compound (VII) is reacted with the phosphine (as described in the first and second methods above) and is precondensed at the same time or subsequently in the presence of an amount of water insufficient for complete hydrolysis, preferably in the presence of 1 to 100 mole % of the amount required for this, for a period of 5 minutes to 48 hours at room temperature to 200° C. Furthermore, independently thereof, the amino silane (X) is precondensed, optionally as a mixture with one or several compounds of formula XI, with or without a solvent, in the presence of an amount of water insufficient for complete hydrolysis, preferably in the presence of 1 to 100 mole % of the amount required for this for a period of 5 minutes to 48 hours at room temperature to 200° C. Thereafter, the two precondensates are combined and then, after the addition of more water and, optionally, more solvent, so that at least the amount of water stoichiometrically necessary for a complete hydrolysis is present, the complete hydrolysis and polycondensation, as well as any further workup in accordance with the first method described above, are carried out.

A further variation on the method of the invention provides that an anhydrous metal component (VII) is reacted with the phosphine component (VIII) in a manner already described, but it is not precondensed. At the same time, but independent of each other, an amino silane (X) and, optionally, one or several compounds (XI) are precondensed with or without a solvent in the presence of an amount of water insufficient for complete hydrolysis, preferably in the presence of 1 to 100 mole % of the amount required for this, for a period of 5 minutes up to 48 hours at room temperature to 200° C. The nonprecondensed, metal-containing mixture and the two precondensates are combined with each other and then, after the addition of more water and, optionally, more solvent, so that at least the amount of water stoichiometrically necessary for a complete hydrolysis and polycondensation is present, the complete hydrolysis and polycondensation as well as any further workup in accordance with the first method described above are carried out.

The different types of precondensation co-determines the structures of the polymers subsequently obtained in a decisive manner. The latter, for their part, influence the catalytic properties of the catalysts obtained in this manner and, in addition, the adhesion of the metal or metals on the polymer ligand carrier. Other properties of the catalyst may be changed as well, based on the precondensation.

This also applies to a fifth method of the invention, according to which a hydrous or anhydrous metal compound (VII) in a preferably polar solvent is reacted with a phosphine (VIII) in the presence of an amino silane (X) as well as, optionally, one or several of the compounds (XI) for a period of 1 minute to 48 hours (in accordance with the first and second methods described above) and an amount of water sufficient at least for the complete hydrolysis and condensation is added to the solution under agitation, and then the procedures or variants described in the first method above are followed.

Of course, a purposeful precondensation can also be carried out in this method, for example, in order to compensate a different gelling behavior of the components, in such a manner that a precondensation is carried out during the reaction of the components to the monomeric metal complex (i.e., reacting compound VII in a polar solvent with the phosphine VIII in the presence of an amino silane X and, optionally, at least one of the compounds XI for 1 minute to 48 hours) or immediately thereafter by means of the addition of an amount of water insufficient for complete hydrolysis, preferably of 1 to 100 mole % of the amount required for this, for a period of 5 minutes up to 48 hours at room temperature to 200° C., and then, after the addition of more water and, optionally, more solvent, so that at least the amount of water stoichiometrically necessary for a complete hydrolysis and polycondensation is present, the complete hydrolysis and polycondensation are carried out, as described in the first method above.

A special variation of the method in accordance with this invention which results in the preparation of polymeric, formed, heterogenized complex catalysts in which, according to formula VI, $X=H$ or the metal is present complex-bound in zero-valent form, provides for a treatment of the monomeric metal complex (preferably prepared in accordance with one of the methods of this invention) before or after an optionally performed precondensation with a reducing agent, optionally at elevated temperature and/or superpressure for a period of 1 minute to 48 hours and follows with the further hydrolysis, polycondensation and workup, as described in the first method above.

Suitable reducing agents include, for example, formaldehyde, hydrazine, alkali- or alkaline-earth metal boron hydride, borane compounds, formates, aluminum hydrides and also alcohols or hydrogen. Moreover, in addition to the reducing agent, a separate acid acceptor can also be added to the solution containing metal complex in addition to the already present amine (X) or excess phosphine (VIII). The following are suitable examples: alkali- or alkaline-earth metal hydroxides; alkali-metal- or alkaline-earth metal hydrides; complex boron or aluminum hydrides; alkali- or alkaline-earth metal carbonates or -bicarbonates; and primary, secondary or tertiary amines.

According to a modification of the above method, the monomeric metal complex (preferably prepared in accordance with one of the methods of this invention) is at first hydrolyzed and polycondensed under forming and suspended, before or after at least one of the workup stages (as described in the first method above), in water or a solvent, preferably a lower alcohol or a mixture thereof with water and subjected to a reducing treatment optionally under superpressure. Thus, the reductive treatment is carried out after the formation of the formed complex catalyst (that is, after the addition of the dispersing water as described in the first method above), or also after the extraction of the produced and formed metal complex or also after its drying and optional tempering, namely in suspension with a suitable solvent as suspending agent. Water or a lower alcohol or a mixture of such an alcohol with water preferably is used for this treatment.

An especially important embodiment of all methods of the invention provides that the spherical complex, which is still moist or wet with solvent and water, is subjected to a temperature treatment.

This treatment under "steaming" or digesting conditions also serves primarily to improve the mechanical strength and of the porosity of the formed material and also may be carried out in the last dispersion of the preparation process present, which dispersion contains a liquid phase and the solid product phase, or in water alone. The temperature treatment can also be combined with a reductive treatment.

The embodiment of a post-treatment of the formed complex catalysts obtained, but not dried, which is described above, thus includes subjecting the complex formed in the form of spheres or pellets in the presence of at least the component water or the liquid phase which was present last in the preparation process as vapor or liquid to a temperature treatment for 1 hour to 1 week at temperatures of 50°–300° C., preferably 100°–200° C., optionally under superpressure. An acidic, basic or additional metal-containing catalyst advantageously may be included. This post-treatment can be carried out in conjunction with a reductive treatment. A preferred method is the hydrogen treatment; in addition, mixtures between hydrogen and inert gases may also be used. An especially effective reduction can take place by using sodium boron hydride, or a combination of this agent with $H_2$ is also possible.

The novel, formed polymeric transition-metal complex catalysts are characterized in particular using the quantitative hydrolysis yields, the elementary analyses and by the catalytic behavior, which are complex-specifically comparable in each instance to that of an analogous, homogeneous complex catalyst.

Purely optically, there is no difference between the polymeric catalysts obtained according to the various preparation methods. An important characteristic of the catalysts prepared according to the methods of the invention is the fact that the complex-bound metal is distributed in a homogenously disperse manner, that is, uniformly over the formed particle. In order to make possible the access of the educts to be reacted to the inner catalytic centers, it is necessary that the formed catalysts exhibit suitable physical properties. In addition to a suitable particle diameter of 0.01 to 3.0 mm, preferably 0.05 to 2.0 mm, the preferred properties include a specific surface of greater than 0 to 1000 $m^2/g$, preferably greater than 0 to 700 $m^2/g$, a specific pore volume of 0.01 to 6.5 ml/g as well as a bulk density of 50–1000 g/l, preferably 100 to 800 g/l. The pore diameters range from greater than 0 to 1000 nm. The thermal stability of the formed catalysts is more than 130° C. in air and more than 200° C. under an atmosphere of inert gas, as a function of the formed complex type.

The formed transition-metal complex catalysts of the invention constitute valuable catalysts for chemical reactions such as reactions of hydroformylation, hydrogenation, oligomerization, carbonylation, hydrosilylation, carboxymethylation and isomerization, as well as for reactions of CO or $CO_2$ with $H_2$. Therefore, the corresponding use of the catalyst constitutes a further aspect of the invention.

Metal-specifically, a different suitability of the systems of the inventions for the above-named reactions is apparent thereby in an analogy to homogeneous catalysts. The formed, polymeric metal complex catalysts may be used in suspension or in a fixed bed or in a fluid bed for reactions in liquid or gaseous phase.

DETAILED DESCRIPTION OF THE INVENTION

The invention is explained in more detail below using examples of corresponding to various particular embodiments of the invention. These examples are intended to be illustrative of the invention and not as limiting the invention.

EXAMPLE 1

Statistical Copolycondensate 14.54 g (0.03 mole) [RhCl($C_8H_{12}$)]$_2$ ($C_8H_{12}$=cyclooctadiene) and 76.9 g (0.18 mole) ($C_6H_5$)P[($CH_2$)$_3$Si(OCH$_3$)$_3$]$_2$ were combined in 100 ml ethanol. The mixture was heated in a 4 liter glass container with agitator and reflux condenser to reflux temperature and agitated 1 hour at this temperature. Then, 223.1 g (0.35 mole) N[($CH_2$)$_3$Si(OC$_2$H$_5$)$_3$]$_3$, 250 ml ethanol and 73.8 g (0.35 mole) Si(OC$_2$H$_5$)$_4$ were added to the mixture. The clear solution was reheated to the reflux temperature and then compounded with 100 ml desalinated water.

It was agitated 10 minutes more under reflux. Then cooled down to 75° C. and agitated further until the start gelling. Two minutes after the start of gelling, 750 ml octanol-1 were added to the mixture and after a further 5 minutes, 700 ml desalinated water were added. The 2-phase mixture was heated under agitation (500 rpms) back to the reflux temperature, agitated 2 hours at this temperature, then cooled down and transferred into a 4 liter pressure container. The suspension was slowly agitated 24 hours at 130° C. and an inherent pressure of approximately 8 bars, then cooled down again and the liquid phase removed by suction from the reddish brown solid present in the form of small spheres. After two extractions with 2 liters ethanol each time, the product was transferred into a drying oven and first dried for 8 hours at 80° C. and then dried for 16 hours at 130° C. under an atmosphere of $N_2$. 187 g (approximately 100% of theory) of a formed, polymeric rhodium complex catalyst was obtained having polymer units of the formula RhCl{($C_6H_5$)P[($CH_2$)$_3$SiO$_{3/2}$]$_2$. 2N[($CH_2$)$_3$SiO$_{3/2}$]$_3$. 2SiO$_2$}$_3$.

of which 98% exhibited a grain size of 0.1 to 1.4 mm.

| Specific surface: | | 558 $m^2/g$ | | |
|---|---|---|---|---|
| Specific total pore volume: | | 2.7 ml/g | | |
| Bulk density: | | 377 g/l | | |
| Elementary analyses: | % Rh | % Cl | % P | % Si |
| Theory: | 3.3 | 1.1 | 2.9 | 26.6 |
| Observed: | 3.2 | 1.0 | 2.8 | 26.4 |

EXAMPLE 2

Mixed Copolycondensate 1.66 g (0.005 mole) RhCl$_3$(CH$_3$CN)$_3$ and 51.9 g (0.1 mole) ($C_6H_5$)P[($CH_2$)$_3$Si(OC$_2$H$_5$)$_3$]$_2$ were combined in 100 ml ethanol. The mixture was heated to reflux temperature and compounded with 5 ml desalinated water. The solution was agitated one hour at this temperature, then compounded with 63.0 g (0.1 mole) N[($CH_2$)$_3$Si(OC$_2$H$_5$)$_3$]$_3$ as well as with a further 20 ml water and agitated 15 minutes further under reflux. The resulting mixture was cooled down to 70° C. and agitated at this temperature at 50 rpms until the start of gelling. Immediately after the start of gelling, 180 ml xylene (industrial mixture) was added to the forming gel and after one more minute 300 ml water was added. The 2-phase system was agitated 1 hour under reflux, then cooled down and transferred into a 3 liter pressure container. The suspension was maintained at 140° C. for 48 hours and then dried analogously to Example 1 and tempered for an additional 12 hours at 160° C. 60.2 g of a formed, polymeric rhodium complex catalyst was obtained having polymer units of the formula $$RhCl_3\{(C_6H_5)P[(CH_2)_3SiO_{3/2}]_2 \cdot N[(CH_2)_3SiO_{3/2}]_3\}_{20},$$

of which 96% exhibited a grain size of 0.2 to 1.6 mm.

| Specific surface: | 478 m²/g | | |
|---|---|---|---|
| Specific total pore volume: | 1.8 ml/g | | |
| Bulk density: | 360 g/l | | |
| Elementary analyses: | % Rh | % Cl | % P |
| Theory: | 0.85 | 0.88 | 5.1 |
| Observed: | 0.8 | 0.8 | 5.0 |

EXAMPLE 3

Block Copolycondensate 0.88 g (0.002 mole) [Rh(O$_2$CCH$_3$)$_2$]$_2$, 54.7 g (0.1 mole) (C$_6$H$_5$)P[CH$_2$Si(OC$_3$H$_7$)]$_2$ and 7.4 g (0.05 mole) (CH$_3$)$_2$Si(OC$_2$H$_5$)$_2$ were combined in 70 ml isopropanol. The solution was compounded with 5 ml desalinated water, heated to reflux temperature and agitated 2 hours under reflux. Parallel thereto, 24.1 g (0.05 mole) HN[(CH$_2$)$_8$Si(OCH$_3$)$_3$]$_2$ and 5 ml 1% aqueous NH$_3$ solution were combined in 50 ml isopropanol and also agitated 2 hours under reflux. Then, the two precondensates were combined, 15 ml water added and the mixture agitated further under reflux until the start of gelling. Ten minutes after the start of gelling, 200 ml sec.-butanol was added and after an additional 30 minutes, 150 ml desalinated water was added. The 2-phase system was agitated a total of 10 hours under reflux, then cooled down and the solid separated from the liquid phase. After a drying step as in Example 2, 45.5 g (99.8% of theory) of a polymeric complex catalyst was obtained having polymer units of the formula $$Rh(O_2CCH_3)_2\{(C_6H_5)P[[CH_2\text{-}SiO_{3/2}]_2 \cdot 0.5HN[(CH_2)_8SiO_{3/2}]_2 \cdot 0.5(CH_3)_2SiO_{2/2}\}_{25},$$

with a grain size distribution of 0.2 mm to 2.0 mm.

| Specific surface: | 152 m²/g | | |
|---|---|---|---|
| Specific total pore volume: | 0.5 ml/g | | |
| Bulk density: | 510 g/l | | |
| Elementary analyses: | % Rh | % P | % Si |
| Theory: | 0.9 | 6.8 | 21.5 |
| Observed: | 0.9 | 6.2 | 20.8 |

EXAMPLE 4

15.7 g (0.09 mole) PdCl$_2$, 76.9 g (0.18 mole) (C$_6$H$_5$)P[(CH$_2$)$_3$Si(OCH$_3$)$_3$]$_2$ and 73.7 g (0.35 mole) Si(OC$_2$H$_5$)$_4$ were combined in 300 ml methanol. The mixture was heated to reflux temperature and agitated at first under reflux until all PdCl$_2$ had dissolved. Then, 10 ml water was added to the solution and the mixture precondensed under agitation at reflux temperature for 1 hour. Then, 178.3 g (0.35 mole) N[(CH$_2$)$_3$Si(OCH$_3$)$_3$]$_3$, as well as an additional 100 ml water were added and the mixture agitated for an additional 15 minutes under reflux. Then, the solution was cooled down to 50° C., agitated further at this temperature until the start of gelling. Immediately after the start of gelling, 400 ml of 2-ethylhexanol was added to the forming gel, and after a further 10 minutes, 600 ml water was added. The 2-phase system was reheated to reflux temperature and agitated 2 hours at this temperature. After proceeding further, as described in the method of Example 1, with the additional difference of a 48 hour post-treatment at 140° C., 193.1 g (99.3% of theory) of a formed, polymeric palladium complex catalyst was obtained having polymer units of the formula $$PdCl_2\{(C_6H_5)P[(CH_2)_3SiO_{3/2}]_2 \cdot 2N[(CH_2)_3SiO_{3/2}]_3 \cdot 2SiO_2\}_2.$$

95% of the formed spheres exhibited a diameter of 0.3 to 1.8 mm.

| Specific surface: | 535 m²/g | | |
|---|---|---|---|
| Specific total pore volume: | 5.8 ml/g | | |
| Mesopore volume: | 3.1 ml | | |
| Macropore volume: | 2.7 ml | | |
| Bulk density: | 225 g/l | | |
| Elementary analyses: | % Pd | % P | % N |
| Theory: | 4.8 | 2.8 | 2.6 |
| Observed: | 4.6 | 2.7 | 2.5 |

EXAMPLE 5

2.94 g (0.01 mole) Na$_2$PdCl$_4$, 20.75 g (0.04 mole) (C$_6$H$_5$)P[(CH$_2$)$_3$Si(OC$_2$H$_5$)$_3$]$_2$, 17.03 g (0.04 mole) HN[(CH$_2$)$_3$Si(OC$_2$H$_5$)$_3$]$_2$ and 16.51 g (0.08 mole) C$_3$H$_7$Si(OC$_2$H$_5$)$_3$ were combined in 60 ml ethanol. The mixture was heated in a 0.5 liter glass container to reflux temperature and agitated for 30 min. at this temperature. 50 ml hexanol-1 and 15 ml water were added, the solution then cooled down to 40° C. and agitated further until the start of gelling. Immediately after the start of gelling, an additional 60 ml hexanol was added and after half a minute of homogenizing, 120 ml water was added. The 2-phase system was heated to reflux temperature and agitated 3 hours at this temperature. The mixture was then cooled down and the formed polymer complex filtered off from the liquid phase and washed twice with 300 ml ethanol each time. After an 8 hour drying at 100° C. and a 16 hour drying at 140° C. under an atmosphere of N$_2$, 29.2 g (99.4% of theory) of a polymeric complex was obtained having units of the formula $$PdCl_2\{(C_6H_5)P[(CH_2)_3SiO_{3/2}]_2 \cdot HN[(CH_2)_3SiO_{3/2}]_2 \cdot 2C_3H_7SiO_{3/2}\}_4$$

97% of the spheres formed exhibited a diameter of 0.6 to 2.4 mm.

| Specific surface: | 246 m²/g | |
|---|---|---|
| Bulk density: | 425 g/l | |
| Elementary analyses: | % Pd | % P |
| Theory: | 3.6 | 4.2 |
| Observed: | 3.5 | 4.2 |

EXAMPLE 6

Precondensation without the addition of water-only with water of crystallization 22.26 g (63.2 mmoles) $IrCl_3.3H_2O$ was dissolved in a 3 liter glass container with double-jacket heating, KPG agitator and reflux cooler in 500 ml ethanol under an argon atmosphere at 60° C. The clear solution was first compounded with 82.4 g (189.5 mmoles) $(C_6H_5)P[(CH_2)_3Si(OCH_3)_3]_2$ and after 5 min. with 39.5 g (189.5 mmoles) $Si(OC_2H_5)_4$ and subsequently agitated for a period of 1 hour at reflux temperature, at which time the reaction and precondensation took place simultaneously. Then, 39.5 g $Si(OC_2H_5)_4$, 238.8 g (379.0 mmoles) $N[(CH_2)_3Si(OC_2H_5)_3]_3$ and 130 ml water were added once more. After 10 minutes of further agitation under reflux temperature, the solution was cooled down to 70° C. and agitated further at this temperature at 100 rpms until the start of gelling.

Immediately after the start of gelling, 700 ml octanol-1 heated to 60° C. was added to the forming gel and the agitation speed was raised to 750 rpms. After a further minute of homogenizing, 1200 ml water in which 1.2 g polyvinyl alcohol (available under the trademark Moviol) had been dissolved was added to the viscous solution. The 2-phase system was heated to the reflux temperature and agitated an additional two hours at this temperature. After the system had cooled off, the solid present in the form of small yellow spheres and the mother solution were separated by decanting, and the solvent-moist solid and mother solution were divided into two equal parts. One half of the named solid, as well as one half the amount of mother solution, were transferred into a 5 liter autoclave (for further processing of the other product half, see Example 7) and agitated under stirring at a temperature of 135° C. for a period of 48 hours under inherent pressure. The mixture was cooled off, the liquid phase removed from the solid by suction and the latter washed twice with 1 liter ethanol each time. The mixture was then dried for 12 hours at 100° C. and for an additional 12 hours at 130° C. under an atmosphere of $N_2$.103 g (98% of theory) product was obtained, of which over 98% was present in the form of yellow spheres with a sphere diameter of 50 μm to 0.6 mm.

| Elementary analyses: | % Ir | % P | % H | % C | % Cl | % Si |
|---|---|---|---|---|---|---|
| Theory: | 5.78 | 2.79 | 4.8 | 32.5 | 3.2 | 25.3 |
| Observed: | 5.7 | 2.68 | 4.7 | 31.7 | 3.1 | 24.8 |

| | |
|---|---|
| Bulk density: | 230 g/l |
| Specific surface: | 540 m²/g |
| Pore volume (pore diameter greater than 2 nm): | 5.4 ml/g |
| Formula for polymer unit: | |
| $IrCl_3\{(C_6H_5)P[(CH_2)_3SiO_{3/2}]_2.2N[(CH_2)_3SiO_{3/2}]_3.2SiO_2\}_3$ | |

EXAMPLE 7

The second half of the polymeric product prepared in Example 6 was subjected to a reductive treatment with sodium boron hydride. To this end, the formed, solvent-moist solid was transferred together with the second half of the mother solution into an autoclave and 40 g $NaBH_4$ was added. The immediately formed hydrogen was first let off, and the solvent moist, solid mixture was rinsed twice with argon. The mixture was then heated to 140° C., during which a pressure of 30 bars developed. The mixture was agitated 24 hours at this temperature. After cooling the mixture and removal of the liquid phase by suction, the mixture was washed twice with 1 liter ethanol each time, twice with 1 liter water each time and twice again with 1 liter ethanol each time. Then, the bright yellow solid was dried for 12 hours at 100° C. as well as for an additional 12 hours at 130° C. under an atmosphere of $N_2$.100 g polymer complex was obtained having polymer units of the formula $IrH_3\{(C_6H_5)P[(CH_2)_3SiO_{3/2}]_2.2N[(CH_2)_3SiO_{3/2}]_3.2SiO_2\}_3$.

98% of the product obtained was present in the form of spheres with a diameter of 50 μm to 0.6 mm.

| Bulk density: | 200 g/l | | |
|---|---|---|---|
| Elementary analyses: | % Ir | % P | % Cl |
| Theory: | 5.9 | 2.9 | 0.0 |
| Observed: | 5.8 | 2.9 | 0.01 |
| Specific surface: | 498 m²/g | | |

EXAMPLE 8

17.49 g (63.2 mmoles) $RuCl_3.3H_2O$ were dissolved in 125 ml ethanol at 60° C., then combined with 82.4 g (189.6 mmoles) $(C_6H_5)P[(CH_2)_3Si(OCH_3)_3]_2$ and with 5 ml water. The solution was then precondensed for a period of 2 hours at reflux temperature under agitation. Parallel thereto, 164.8 g (379.0 mmoles) $Si(OC_2H_5)_4$, dissolved in 50 ml ethanol, was precondensed by reaction with 5 ml water, and also 238.8 g (379.0 mmoles) $N[(CH_2)_3Si(OC_2H_5)_3]_3$, dissolved in 200 ml ethanol, was precondensed by reaction with 8 ml water for a period of 2 hours at reflux temperature under agitation in each instance. Thereafter, all three precondensates were combined in a 3 liter glass container with double-jacket heating, KPG agitator and reflux cooler, the mixture was compounded with an additional 50 ml water and agitated again for 10 minutes under reflux. Thereafter, the mixture was cooled down to 70° C. and agitated further until the start of gelling. Five minutes after the start of gelling, 700 ml octanol was added to the forming gel and after an additional 2 minutes, 1300 ml water was added. The 2-phase system was reheated to the reflux temperature and agitated for 1 hour at this temperature. Thereafter, the batch was cooled down and the formed solid as well as the mother solution were divided into two equal parts each. One part thereof was transferred into a 5 liter autoclave and agitated 24 hours in it at 150° C. After cooling off the mixture, removal of the liquid phase, triple extraction of the yellow solid with 500 ml ethanol each time and an 8 hour drying at 110° C. as well as a 12 hour drying at 140° C., 101 g (98% of theory) polymer complex was obtained having polymer units of the formula $RuCl_3\{(C_6H_5)P[(CH_2)_3SiO_{3/2}]_2.2N[(CH_2)_3SiO_{3/2}]_3.2SiO_2\}_3$.

95% of the product obtained was present in the form of spheres with a diameter of 0.1 to 0.8 mm.

| Bulk density: | 300 g/l |
|---|---|
| Total pore volume: | 3.4 ml/g (pore diameter: 2 to 1000 nm) |

Elementary

-continued

| analyses: | % Ru | % P | % H | % C | % Cl | % Si | % N |
|---|---|---|---|---|---|---|---|
| Theory: | 3.1 | 2.9 | 5.0 | 33.4 | 3.3 | 26.0 | 2.6 |
| Observed: | 3.1 | 2.8 | 4.9 | 33.2 | 3.2 | 25.7 | 2.4 |

EXAMPLE 9

The other half of the spherical, still solvent-moist raw product prepared in Example 8 was transferred together with the other half amount of mother solution into an autoclave and then compounded with 20 g sodium boron hydride. After a process analogous to that of Example 7, 98.8 g (99.9% of theory) polymer complex was obtained having units of the formula $RuH_2\{(C_6H_5)P[(CH_2)_3SiO_{3/2}]_2 \cdot 2N[(CH_2)_3Si-O_{3/2}]_3 \cdot 2SiO_2\}_3$.

| | Bulk density: | | | 180 g/l | | | |
|---|---|---|---|---|---|---|---|
| Elementary analyses: | % Ru | % P | % H | % C | % Cl | % Si | % N |
| Theory: | 3.2 | 3.0 | 5.1 | 34.5 | 0 | 26.9 | 2.7 |
| Observed: | 3.0 | 2.9 | 5.0 | 34.2 | 0.1 | 26.3 | 2.6 |

EXAMPLE 10

36.1 g (95 mmoles) $(NH_4)_2 PtCl_4$, 164.8 g (380 mmoles) $(C_6H_5) P[(CH_2)_3Si(OCH_3)_3]_2$ and 158.3 g (760 mmoles) $Si(OC_2H_5)_4$ were combined in a 3 liter autoclave in 400 ml ethanol. The mixture was first agitated 1 hour at 100° C., then compounded with 15 g 35% $N_2H_4$ solution as well as 6.6 g NaOH and agitated an additional 2 hours at 120° C. Thereafter, the solution was transferred into a glass container with a KPG agitator and a reflux cooler and compounded with 119.6 g (190 mmoles) $N[(CH_2)_3Si(OC_2H_5)_3]_3$ and an additional 120 ml water and cooled down to 65° C. The mixture was agitated further at this temperature until the start of gelling. Immediately after the start of gelling, 650 ml octanol was added, and after an additional 6 minutes, 800 ml water was added. The mixture was agitated one half hour more at the reflux temperature at 500 rpms and then the entire suspension was transferred into an autoclave. After a 24 hour post-treatment at 150° C., the solid was extracted twice with 1 liter ethanol each time and twice with 1 liter water each time, and then dried 24 hours at 120° C., and under 100 mbars pressure. 231 g (99% of theory) polymer complex was obtained having polymer units of the formula $Pt\{(C_6H_5)P[(CH_2)_3SiO_{3/2}]_2 \cdot 0.5N[(CH_2)_3SiO_{3/2}]_3 \cdot 2SiO_2\}_4$.

95% of the product present in the form of spheres exhibited a particle diameter of 0.3–2.0 mm.

| | Bulk density: | | 190 g/l | |
|---|---|---|---|---|
| Elementary analyses: | % Pt | % Cl | % P | % Si | % N |
| Theory: | 7.9 | 0 | 5.0 | 25.2 | 1.1 |
| Observed: | 7.7 | 0.1 | 4.8 | 25.0 | 1.0 |

EXAMPLE 11

13.5 g (50 mmoles) $FeCl_3 \cdot 3H_2O$ and 96.4 g (150 mmoles)

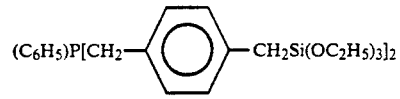

were dissolved in 500 ml ethanol. The solution was agitated one hour under reflux, then compounded with 377.9 g (750 mmoles) $N[(CH_2)_3Si(OCH_3)_3]_3$ and 140 ml water. The mixture was agitated further under reflux until the start of gelling. Immediately after the gelling, 1000 ml 2-ethylhexanol was added and, after one more minute of homogenizing, 10.6 g (50 mmoles) $(H_5C_2)Ti(OC_2H_5)_3$ as well as 1000 ml water were added. The 2-phase system was agitated for 2 hours further under reflux, then cooled down, the liquid phase removed by suction and the remaining solid extracted three times with 1 liter ethanol each time. After an 8 hour drying at 100° C. and a 12 hour drying at 130° C., as well as a 12 hour drying at 160° C. under an atmosphere of $N_2$, 295 g (98.8% of theory) of formed polymer product was obtained having units of the formula

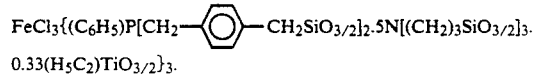

Sphere size ($d_{95\%}$): 0.3–2.4 mm
Bulk density: 430 g/l

| Elementary analyses: | % Fe | % P | % N | % Ti |
|---|---|---|---|---|
| Theory: | 0.94 | 1.56 | 3.5 | 0.8 |
| Observed: | 0.86 | 1.5 | 3.4 | 0.9 |

EXAMPLE 12

Starting with 12.5 g (50 mmoles) $Co(O_2CCH_3)_2 \cdot 4 \cdot H_2O$, 56.8 g (150 mmoles) $(C_6H_5)P[CH_2-Si(OCH_3)_3]_2$ and 377 g (750 mmoles) $N[(CH_2)_3Si(OCH_3)_3]_3$ as well as 7.4 g (30 mmoles) $Al(OC_4H_9)_3$ and using the same solvent and amounts of solvent and the same method as in Example 11, 269 g polymer complex was obtained having polymer units of the formula $Co(O_2CCH_3)_2\{(C_6H_5)P[CH_2-SiO_{3/2}]_2 \cdot 5N[(CH_2)_3SiO_{3/2}]_3 \cdot 0.2AlO_{3/2}]_3\}$.

| Sphere size ($d_{98\%}$): | | 0.2–1.8 mm | | |
| Bulk density: | | 350 g/l | | |
|---|---|---|---|---|
| Elementary analyses: | % Co | % P | % N | % Al |
| Theory: | 1.1 | 1.7 | 3.9 | 0.3 |
| Observed: | 1.1 | 1.6 | 3.8 | 0.3 |

EXAMPLE 13

Starting with 13.1 g (50 mmoles) $NiSO_4 \cdot 6H_2O$, 25.9 g (50 mmoles) $(C_6H_5) P[(CH_2)_3Si(OC_2H_5)_3]_2$ and 630.06 g (1.0 mmole) $N[(CH_2)_3Si(OC_2H_5)_3]_3$ as well as 19.2 g (50 mmoles) $Zr(OC_4H_9)_4$ and using diisopropyl ether instead of 2-ethylhexanol and using the same method as in Example 11, 324.6 g polymer complex was obtained having units of the formula

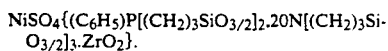
NiSO$_4${(C$_6$H$_5$)P[(CH$_2$)$_3$SiO$_{3/2}$]$_2$.20N[(CH$_2$)$_3$Si-O$_{3/2}$]$_3$.ZrO$_2$}.

| Sphere size (d$_{98\%}$): | | 0.1–1.6 mm | |
|---|---|---|---|
| Bulk density: | | 510 g/l | |
| Elementary analyses: | % Ni | % P | % N | % Zr |
| Theory: | 0.9 | 0.48 | 4.3 | 1.4 |
| Observed: | 0.9 | 0.4 | 4.2 | 1.2 |
| Pore volume: | | 0.6 ml/g | |
| (exclusively pores with a diameter less than 2 nm) | | | |

EXAMPLE 14

Starting with 3.0 g (10 mmoles) OsCl$_3$, 217.3 g (500 mmoles) (C$_6$H$_5$) P[(CH$_2$)$_3$Si(OCH$_3$)$_3$]$_2$, as well as 251.9 g (500 mmoles) N[(CH$_2$)$_3$Si(OCH$_3$)$_3$]$_3$, and using 1-hexanol instead of 2-ethylhexanol, as well as using methanol instead of ethanol, and practicing the same method as in Example 11, but eliminating the addition of the cross-linking agent, 298.0 g of a polymer complex was obtained having units of the formula

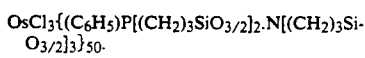
OsCl$_3${(C$_6$H$_5$)P[(CH$_2$)$_3$SiO$_{3/2}$]$_2$.N[(CH$_2$)$_3$Si-O$_{3/2}$]$_3$}$_{50}$.

| Sphere size (d$_{98\%}$): | | 0.1–1.4 mm | |
|---|---|---|---|
| Bulk density: | | 400 g/l | |
| Elementary analyses: | % Os | % P | % N | % Si |
| Theory: | 0.64 | 5.2 | 2.3 | 23.5 |
| Observed: | 0.6 | 5.0 | 2.2 | 23.2 |

EXAMPLE 15

The batch for producing the polymer complex

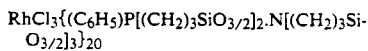
RhCl$_3${(C$_6$H$_5$)P[(CH$_2$)$_3$SiO$_{3/2}$]$_2$.N[(CH$_2$)$_3$Si-O$_{3/2}$]$_3$}$_{20}$ according to Example 2 was repeated. After the conclusion of the reflux phase and the obtention of the xylene-moist, formed raw product, the 2-phase system was transferred as in Example 2 into a 3 liter pressure container. At first, 50 bars CO and then 50 bars H$_2$ were pressed onto the pressure container. The mixture was then heated under agitation to 140° C. and maintained at this temperature for 30 hours. Then it was cooled down, the pressure removed and it was worked up as in Example 2. After drying, the product was washed with 3 liters NaOH solution (pH 12) and with 2 liters water and redried 12 hours at 120° C. 59.8 g of a formed, polymeric rhodium complex catalyst was obtained having polymer units of the formula

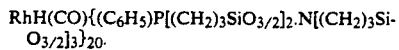
RhH(CO){(C$_6$H$_5$)P[(CH$_2$)$_3$SiO$_{3/2}$]$_2$.N[(CH$_2$)$_3$Si-O$_{3/2}$]$_3$}$_{20}$.

| Sphere size (d$_{98\%}$): | | 0.2–1.6 mm | |
|---|---|---|---|
| Specific pore volume: | | 1.9 ml/g | |
| Bulk density: | | • 330 g/l | |
| Elementary analyses: | % Rh | % Cl | % P | % N |

| -continued | | | | |
|---|---|---|---|---|
| Theory: | 0.86 | 0 | 5.2 | 2.3 |
| Observed: | 0.8 | 0.15 | 5.1 | 2.2 |
| IR spectrum: | $\nu$ CO | approximately 1950 cm$^{-1}$ | | |
| | $\nu$ H | approximately 2050 cm$^{-1}$ | | |

EXAMPLE 16

50 ml of the Rh-containing polymer complex prepared in Example 1 with a grain size of 0.3 to 1.2 mm were filled into a tubular reactor with an inside diameter of 16 mm. The tubular reactor was built into a continuous hydroformylation apparatus. After the system had been started up and constant conditions had been adjusted after 48 hours of operation, the hydroformylation of octene-1 was carried out under the following conditions:

| Total pressure | 200 bars |
|---|---|
| H$_2$/CO ratio | 1:1 |
| Temperature in the reactor | 100° C. |
| Volumetric rate of flow octene-1 | 50 ml/h |
| Gas flow H$_2$/CO | 100 Nl/h |

A gas-chromatic analysis (GC analysis) of the product which had been discharged and relieved of pressure yielded a composition of 97.5% total aldehyde content (remainder: olefine isomers, octane) at an n:i product ratio of 2. The Rh content of the product was less than 0.05 ppm. After 200, 400 and 600 hours of operation, GC analyses of the product were again performed. Approximately the same composition resulted thereby, and the presence of rhodium was no longer able to be demonstrated by means of atom absorption.

EXAMPLE 17

5.0 g of the Pd-containing polymer complex prepared in Example 4 with a grain size of 0.3–0.6 mm was combined with 234 g vinyl cyclohexene in a 1 liter autoclave. A constant pressure of 5 bars H$_2$ was put on the autoclave and the hydrogen consumed was continuously replenished from a reservoir. The mixture was then heated under agitation (1000 rpms) to 60° C. and agitated further (approximately 5 hours) until the theoretical amount of hydrogen required for the hydrogenation of a double bond had been consumed. The mixture was then cooled down and a GC analysis of the product mixture performed. According to this analysis, approximately 90% of the educt amount used had been hydrogenated to ethylcyclohexene.

EXAMPLE 18

5.0 g of the Ir-containing polymer complex prepared in Example 7 with a grain size of 50 μm to 0.2 mm was combined with 166.2 g tetrahydrobenzaldehyde in a 1 liter autoclave. The autoclave was loaded with 10 bars hydrogen and the consumed hydrogen was continuously replenished from a reservoir. The mixture was heated under agitation (1000 rpms) to 70° C. and agitated further (approximately 7 hours) until the theoretical amount of hydrogen required for the hydrogenation of a double bond had been consumed. A GC analysis of the product obtained showed that 95% of the educt used had been converted to tetrahydrobenzyl alcohol.

EXAMPLE 19

5 g of the Pt-containing polymer complex prepared in Example 10 with a grain size of 0.3-0.8 mm was combined with 221.5 g octene-1 and 267.3 g HSiCl$_3$ in a 1 liter glass autoclave. The reaction mixture was heated under agitation (1000 rpms) to 100° C. and maintained at this temperature for 24 hours. A GC analysis of the product obtained showed that 95% of the octene-1 used had been converted to octyltrichlorosilane.

While this invention has been described in connection with various particular examples, these examples are intended to be illustrative of the invention and not limiting the same. Those skilled in the art will recognize that various modifications and changes may be made without departing from the spirit and scope of the invention as defined in the appended claims.

The priority document, German Patent Application No. P 40 35 032.0, filed in Germany on Nov. 3, 1990, is entirely relied on an incorporated herein by reference.

Also entirely incorporated herein by reference is the related U.S. patent application Ser. No. 07/786,796, filed on Nov. 1, 1991, related to German Patent Application No. P 40 35 033.9, filed in Germany on Nov. 3, 1990.

We claim:

1. A formed, polymeric metal complex of iron, cobalt, nickel, ruthenium, rhodium, palladium, osmium, iridium and/or platinum, including a central metal atom and a ligand, wherein the ligand includes a formed organosiloxane copolycondensate having amine units of the formula

 (I)

and phosphine units of the formula

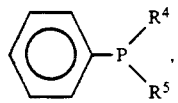 (II)

wherein the central atom is coordinatively bound via a strongly bonding phosphorus atom of the phosphine units and/or, via a more weakly bonding nitrogen atom of the amine units, wherein R$^2$ to R$^5$ are the same or different and signify a group of the formula

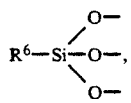 (III)

in which R$^6$ is bound directly to the phosphorus atom or to the nitrogen atom and represents a linear or branched alkylene group with 1 to 10 carbon atoms, a cycloalkylene group with 5 to 8 carbon atoms or a unit of the formula

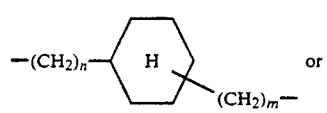

or

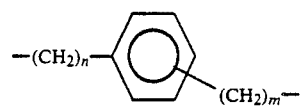

wherein n and m each are numbers from 0 to 6, n represents the number of methylene groups bound to an N position or bound to a P position and m represents the number of methylene groups bound to an Si position, wherein R$^1$ represents a group of formula (III) or H, CH$_3$, C$_2$H$_5$, C$_3$H$_7$, wherein the free valences of the oxygen atoms bound to the Si atom are saturated as in silica skeletons by silicon atoms of further groups of formula (III) and/or via the metal atoms in one or several cross-linking bridge members

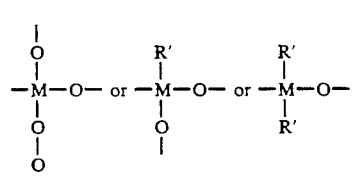 (IV)

and/or

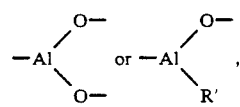

wherein M is an Si, Ti or Zr atom and R' is a linear or branched alkyl group having 1 to 5 carbon atoms or a phenyl group, and the ratio of the silicon atoms from the groups of formula (III) to the metal atoms in the cross-linking bridge members (IV) is 1:0 to 1:20, and the ratio between the number of moles of phosphine units (II) and the number of totally complex-bound metal units is 1:1 to 1000:1, and wherein the polymeric complex catalyst is present macroscopically as spherical particles having a diameter of 0.01 to 3.0 mm, having a specific surface of greater than 0 to 1000 m$^2$/g, having a specific pore volume of 0.01 to 6.5 ml/g and a bulk density of 50 to 1000 g/l.

2. The formed, polymeric metal complex according to claim 1, wherein the ratio of the units according to formula (I) to the units according to formula (II) is 5:95 to 95:5 mole %.

3. The formed, polymeric metal complex according to claim 1, wherein R$^1$ to R$^5$ are a group of the formula (III) and are identical or different.

4. The formed, polymeric metal complex according to claim 1, wherein the complex is present as a statistical copolycondensate, a block copolycondensate or a mixed copolycondensate.

5. The formed, polymeric metal complex according to claim 1, wherein R$^1$ to R$^5$ represent a group having the formula

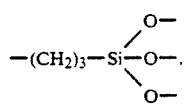 (V)

6. The formed, polymeric metal complex according to claim 1, wherein one or several units of formula (VI) are chosen from the group consisting of $FeX_3$, $FeX_2$, $CoX_3$, $CoX_2$, $NiX_2$, $RuX_3$, $RuX_2$, $RhX_3$, $RhX_2$, $RhX$, $Rh(dien)X$, $RhX(CO)$, $PdX_4$, $PdX_2$, $Pd^0$, $OsX_3$, $IrX_3$, $IrX$, $Ir(dien)X$, $IrX(CO)$, $PtX_4$, $PtX_2$, and $Pt^0$, and are bound to the units of formula (II) and formula (I), in which X represents Cl, Br, I, H, acetyl acetonate, acetate, 0.5 $SO_4$, $NO_3$, and CN, and diene represents cyclooctadiene or norbornadiene.

7. The formed, polymeric metal complex according to claim 6, wherein the units according to formula (VI) are each bound via at least one phosphine unit according to formula (II) to a polymer matrix.

8. The formed, polymeric metal complex according to claim 7, wherein the units according to formula (VI) are bound to the polymer matrix only via phosphine units according to formula (II).

9. The formed, polymeric metal complex according to claim 6, wherein the metal content in the polymer system is at least 0.01% by weight and at the most 20% by weight.

10. The formed, polymeric metal complex according to claim 6, further comprising in addition to the ligands according to formulas (II) and (I) complexing the metal central atoms according to formula (VI), still other excess, non-complexing ligands according to formulas (I) or (II) are present in the polymer system.

11. The formed, polymeric metal complex according to claim 1, wherein ligand units according to formula (II) are present in the polymer system only in the minimum amount that is required to build up a particular metal complex, such that the stoichiometric ratio between the ligands according to formula (II) and the metal is at least 1:1, and a maximum ratio of 4:1, and additional ligands according to formula (I) are present.

12. A method of preparing a formed polymeric metal complex comprising, reacting one or more hydrous or anhydrous metal compounds (VII) chosen from the group consisting of:

$FeX_3$, $FeX_2$, $CoX_3$, $CoX_2$, $NiX_2$, $RuX_3$, $RuX_3(CH_3CN)_3$, $RuX_3(C_6H_5CN)_3$, $M_3RhX_6$, $RhX_3$, $RhX_3(CH_3CN)_3$, $RhX_3(C_6H_5CN)_3$, $RhX_2$, $[RhX(dien)]_2$, $M_2PdX_6$, $M_2PdX_4$, $PdX_2$, $OsX_3$, $OsX_3(CH_3CN)_3$, $OsX_3(C_6H_5CN)_3$, $M_3IrX_6$, $IrX_3$, $IrX_3(CH_3CN)_3$, $IrX_3(C_6H_5CN)_3$, $[IrX(dien)]_2$, $M_2PtX_6$, $M_2PtX_4$, and $PtX_2$, wherein
X represents Cl, Br, I, acetyl acetonate, acetate, $\frac{1}{2}SO_4$, $NO_3$, or CN;
dien represents cyclooctadiene or norbornadiene; and
M represents H, Na, K, or $NH_4$, to form a metal complex in a solvent or a solvent mixture optionally at an elevated temperature, for a period in the range of 1 minute to 48 hours with a phosphine of the formula

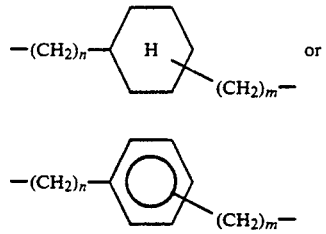

(VIII)

wherein $R^7$ and $R^8$ are identical or different and signify a group having a formula $R^6$—Si(OR$^9$)$_3$   (IX), wherein $R^6$ represents a linear or branched alkylene group with 1 to 10 carbon atoms, a cycloalkylene group with 5 to 8 carbon atoms or a unit of the formula

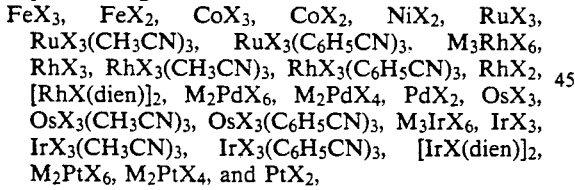

wherein n and m each are numbers from 0 to 6, n represents the number of methylene groups bound to an N position or bound to a P position and m represents the number of methylene groups bound to an Si position, $R^9$ signifies a linear or branched alkyl group with 1 to 5 carbon atoms and the ratio between the number of moles of phosphine according to formula VIII and the number of moles of the total complex bound metal atoms in the metal compounds according to formula VII is in the range of 1:1 to 1000:1, to thereby form a first solution;

adding amino silane of the formula

(X)

wherein $R^{10}$ represent H, $CH_3$, $C_2H_7$ or a group of formula IX and $R^{11}$ and $R^{12}$ represent a group of formula IX in which $R^6$ and $R^9$ have the same meaning as in formula IX, and optionally one or more compounds of the formula $M(OR)_{2-4} R'_{0-2}$ or $M(OR)_{2-3} R'_{0-1}$   (XI), in which M represents an Si, Ti, Zr or Al atom, R' represents a linear or branched alkyl group with 1 to 5 carbon atoms or a phenyl group, R represents a linear or branched alkyl group with 1 to 5 carbon atoms and the ratio of the silicon atoms from the groups of formula IX to the metal atoms in the cross-linking agents XI is 1:0 to 1:20, to the first solution obtained to obtain a second solution;

adding an amount of water to the second obtained solution under agitation, wherein enough water is added to at least complete hydrolysis and condensation to thereby form a reaction mixture;

hydrolyzing the reaction mixture for a period of up to 6 hours, optionally at a reflux temperature;

allowing the reaction mixture to gel under further agitation at a temperature in the range of room temperature to 200° C.;

compounding at the start of gelling or up to one hour thereafter with 10 to 2000% by weight, relative to the entire amount of phosphine (VIII), aminoorganosilane (X) and, optionally, cross-linking agent (XI), with a solvent which is largely non-water-soluble but dissolves the reaction mixture which has gelled or started to gel;

homogenizing the reaction mixture;

adding 10 to 2000% by weight water to the homogenizate, relative to the total amount of phosphine (VIII), aminoorganosilane (X) and, optionally, cross-linking agent (XI), up to 10 hours after homogenization, optionally under elevation of the originally adjusted temperature, wherein an organic phase contains a monomeric metal complex dispersed in a liquid two-phase system;

separating a solid in the form of spheres from the liquid phase after a reaction time sufficient for this purpose at a temperature in the range of room temperature to 200° C.;

then extracting, optionally with a low-boiling solvent;

drying at room temperature to 250° C., optionally under protective gas or in a vacuum, and optionally tempering for 1 to 100 hours at temperatures of 150° C. to 300° C. or classifying according to size.

13. The method according to claim 12, wherein the solvent used in the hydrolysis is at least one member selected from the group of methanol, ethanol, n-propanol, i-propanol, n-butanol, i-butanol or n-pentanol.

14. The method according to claim 12, wherein the hydrolysis is carried out in an excess of water.

15. The method according to claim 12, further comprising adding at least one member selected from the group of a linear or branched alcohol with 4 to 12 carbon atoms, toluene, ethyl benzene, o-xylene, m-xylene or p-xylene to the reaction mixture which has gelled or has started to gel.

16. The method according to claim 12, wherein the gelling and the formation of the solid is carried out at a normal pressure or a superpressure, which normal pressure or superpressure corresponds to the sum of the partial pressures of the components of the reaction mixture at the temperature of the reaction system.

17. The method according to claim 12, wherein at least a portion of the solvent is largely non-water-soluble and is added in the hydrolysis stage in addition to the solvent used in the hydrolysis step.

18. The method according to claim 12, wherein the one or more hydrous or anhydrous metal compounds of formula (VII) are in a polar solvent or solvent mixture, reacting said metal compounds with said phosphine of formula (VIII) at a molar ratio between the number of moles of phosphine units (VIII) and the number of moles of the totally complex-bound metal in the range of 1:1 to 1000:1 for a period of 1 minute to 48 hours; adding at least a portion of the one or several of the compounds of formula (XI) to the solution of the formed, monomeric metal complex; precondensing this mixture in the presence of water, such that the amount of water is insufficient for complete hydrolysis, for a period of from 5 minutes to 48 at a temperature in the range of room temperature to 200° C.; adding an amino silane of forming (X), optionally adding the remaining or complete amount of one or more of the compounds according to formula (XI), optionally adding more solvent, and adding more water; hydrolyzing the mixture again for a period of up to 4 hours, optionally at the reflux temperature of the reaction mixture, to thereby precondense the reaction mixture.

19. The method according to claim 18, wherein the precondensation is carried out in the presence of an acidic, basic or metal-containing condensation catalyst.

20. The method according to claim 18, wherein the precondensation is carried out only with the water introduced by a metal component containing water of crystallization.

21. The method according to claim 18, wherein the amount of water used for precondensation and in excess of an optionally present amount of water of crystallization is added at the start of the reaction of the metal component (VII) with the phosphine (VIII).

22. A method according to claim 12, further comprising reacting the one or more hydrous or anhydrous metal compounds (VII) for a period of 1 minute to 48 hours in a polor solvent or solvent mixture with the phosphine (VIII) in a ratio between the number of moles of phosphine units (VIII) and the number of moles of the totally complex-bound metal atoms of 1:1 to x:1, where x represents the particular metal-specific maximum coordination number in the particular metal complex, to thereby form a reaction mixture;

adding at least a portion of the complete amount of one or more of the compounds (XI) to the reaction mixture;

precondensing the reaction mixture in the presence of an amount of water insufficient for complete hydrolysis, optionally from 1 to 100 mole % of the amount required for complete hydrolysis, for a period of 5 minutes up to 48 hours at a temperature in the range of room temperature to 200° C.;

adding an additional phosphine (VIII) exceeding the maximum coordination number of the metal, optionally the remaining or complete amount of one or more of the compounds (XI), optionally an amino silane (X), optionally more solvent, and water;

hydrolyzing the mixture again for a period of up to 4 hours, optionally at the reflux temperature of the reaction mixture, to thereby precondense the reaction mixture.

23. The method of preparing the formed, polymeric metal complexes according to claim 22, further comprising:

precondensing the monomeric metal complex obtained from the reaction of the metal compound (VII) with the phosphine component (VIII) together with any optionally present, excess phosphine (VIII), during or after its preparation, an amino silane of formula (X), and optionally, one or more compounds of formula (XI) for a period of 5 minutes to 48 hours at a temperature in the range of room temperature to 200° C., independently of one another with an optional solvent, in the presence of 1 to 100 mole % of the amount of water necessary for complete hydrolysis;

combining the individual precondensed components; adding an amount of water such that at least the amount of water stoichiometrically necessary for a complete hydrolysis is present and, optionally, adding additional solvent, to thereby provide the solution for the hydrolysis.

24. The method according to claim 12, further comprising: reacting the metal compound (VII) with the phosphine (VIII) and precondensing at the same time or subsequent to the reacting step in the presence of 1 to 100 mole % of the amount of water necessary for complete hydrolysis, for a period of 5 minutes to 48 hours at a temperature in the range of room temperature to 200° C.; and, independent thereof, precondensing the amino silane (X), optionally as a mixture with at least one compound of formula (XI), optionally with a solvent, in the presence of 1 to 100 mole % of the amount of water necessary for complete hydrolysis, for a period of 5 minutes to 48 hours at a temperature in the range of room temperature to 200° C.;

combining the two precondensates; and adding water and, optionally, solvent, such that at least the amount of water stoichiometrically necessary for a complete hydrolysis is present, to thereby provide the solution for the hydrolysis and polycondensation.

25. The method according to claim 12, further comprising: precondensing the amino silane (X) and, optionally, at least one of the compounds (XI), optionally with a solvent in the presence of 1 to 100 mole % of the amount of water necessary for complete hydrolysis, for a period of 5 minutes up to 48 hours at a temperature in the range of room temperature to 200° C.;

combining a non-precondensed, metal-containing reaction product with the precondensate and adding water and, optionally, solvent, such that at least the amount of water stoichiometrically necessary for a complete hydrolysis and polycondensation is present, to thereby provide the solution for the hydrolysis.

26. The method according to claim 12, wherein before or after an optionally performed precondensation, a reducing treatment with a reducing agent is performed, optionally at an elevated temperature and/or a superpressure, for a period of 1 minute to 48 hours prior to the hydrolysis.

27. The method according to claim 12, further comprising: hydrolyzing and polycondensing the monomeric metal complex and suspending the complex in water or a solvent, optionally a lower alcohol solvent or a mixture thereof with water, and reducing the complex by subjecting said complex to a reducing treatment with a reducing agent, optionally at an elevated temperature for a period of 1 minute to 48 hours, optionally under superpressure.

28. The method according to claim 12, further comprising: post-treating the still solvent-moist and water-moist complex in the presence of water, and optionally, a solvent miscible with water or the last liquid present in the preparation process, wherein the last liquid present in the preparation process may be present in liquid form or in vapor form, wherein the post-treatment includes a temperature treatment for 1 hours to one week at a temperature in the range of 50° to 300° C., optionally under superpressure and optionally under a simultaneous reduction treatment in an atmosphere of hydrogen, or sodium boron hydride or both.

29. The method according to claim 28, wherein the post-treatment is carried out in the presence of an acidic, basic or metal-containing hydrolysis catalyst or a condensation catalyst.

* * * * *